United States Patent
Childers et al.

(10) Patent No.: US 6,518,272 B2
(45) Date of Patent: Feb. 11, 2003

(54) CYCLOALKYL-SUBSTITUTED ARYL-PIPERAZINES, PIPERIDINES AND TETRAHYDROPYRIDINES AS SEROTONERGIC AGENTS

(75) Inventors: Wayne E. Childers, New Hope, PA (US); Michael G. Kelly, Thousand Oaks, CA (US); Yvette L. Palmer, Yardley, PA (US); Edward J. Podlesny, New Tripoli, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/107,866

(22) Filed: Mar. 27, 2002

(65) Prior Publication Data

US 2002/0156075 A1 Oct. 24, 2002

Related U.S. Application Data

(60) Division of application No. 09/723,478, filed on Nov. 28, 2000, now Pat. No. 6,376,494, which is a continuation-in-part of application No. 09/333,158, filed on Jun. 14, 1999, now abandoned.
(60) Provisional application No. 60/135,107, filed on Jun. 15, 1998.

(51) Int. Cl.[7] ...................... A61K 31/50; A61K 31/495; A61K 31/445; A61K 31/44

(52) U.S. Cl. .......................... 514/252.16; 514/253.01; 514/253.05; 514/254.02; 514/254.06; 514/254.1; 514/255.03; 514/331; 514/357

(58) Field of Search ............... 514/252.16, 253.01, 514/253.05, 254.02, 254.06, 254.1, 255.03, 331, 357

(56) References Cited

U.S. PATENT DOCUMENTS

| | | | |
|---|---|---|---|
| 3,717,634 A | 2/1973 | Wu et al. | |
| 4,873,331 A | 10/1989 | Childers et al. | |
| 4,882,432 A | 11/1989 | Abou-Gharbia et al. | |
| 4,988,814 A | 1/1991 | Abou-Charbia et al. | |
| 5,340,812 A | 8/1994 | Cliffe | |
| 5,364,849 A | 11/1994 | Cliffe | |
| 5,486,518 A | 1/1996 | Yardley et al. | |
| 5,519,025 A | 5/1996 | Yardley et al. | |

FOREIGN PATENT DOCUMENTS

| | | |
|---|---|---|
| EP | 0 506 468 | 9/1992 |
| EP | 0 512 755 B1 | 11/1992 |
| WO | WO 93/11122 | 6/1993 |
| WO | WO 94/21610 | 9/1994 |
| WO | WO 95/33743 | 12/1995 |
| WO | WO 96/01656 | 1/1996 |
| WO | WO 97/40038 | 10/1997 |
| WO | WO 99/65887 | * 12/1999 |

OTHER PUBLICATIONS

Rasmussen et al., Annual Rpts. In Med. Chem. vol. 30, pp 1–9 (1995).
Glennon, R.A., Drug Development Res., 26(3) Jan. 1992, pp 251–274.
Sleight, A.J., et al., Naunyn–Schmiedeberg's Archives of Pharmacology, vol. 343, Jan. 1991, pp 109–116.
Cliffe, I.A. et al., Drugs of the Future, 18(7), 1993, pp 631–642.
Nelson, D.L., Pharmacology Biochemistry & Behavior, vol. 40, 1991, pp 1041–1051.
Glennon R. et al., J. Med. Chem., 32(8), Aug. 1989, pp 1921–1926.
Glennon, R. et al., Drug Development Research, 16(2/04), Jan. 1989, pp 335–343.
Kuipers et al., J. Med. Chem. 38 pp1942–1954, 1995.

* cited by examiner

Primary Examiner—William R. A. Jarvis
(74) Attorney, Agent, or Firm—Joseph M. Mazzarese; Kimberly R. Hild

(57) ABSTRACT

This invention relates to compounds which have activity as $5\text{-HT}_{1A}$ agonists and antagonists which may be useful for the treatment of anxiety, depression, cognitive deficits, and prostate cancer, having the formula

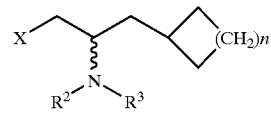

wherein: X is a moiety selected from the group of:

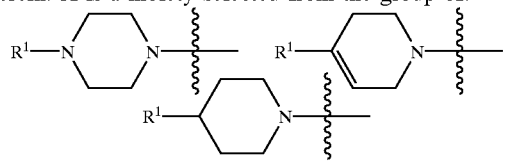

n is selected from the integers 1 through 5; $R^1$ is optionally substituted aryl or mono or bicyclic heteroaryl, with a proviso that heteroaryl is not thiadiazole; $R^2$ is H or alkyl; $R^3$ is H, $COR^5$, $COOR^5$, and $CONR^5R^6$; $R^4$ is H, alkyl, alkenyl, alkynyl, aryl, mono or bicyclic heteroaryl, aralkyl, and mono or bicyclic heteroaralkyl, wherein the aryl or heteroaryl groups are optionally substituted; $R^5$ and $R^6$ are H, alkyl, alkenyl, alkynyl, cycloalkyl, cycloalkenyl, adamantyl, and noradamantyl or $R^5$ and $R^6$ taken together may form a 5–7 membered azacyclic ring, optionally containing an additional heteroatom selected from O, S, or $NR^4$; when $R^5$ or $R^6$ are chosen from cycloalkyl or cycloalkenyl, the cyclic group may optionally be substituted at the 1-position with a $C_1$–$C_3$ alkyl group;
or an optical isomer; or a pharmaceutically acceptable salt thereof.

12 Claims, No Drawings

CYCLOALKYL-SUBSTITUTED ARYL-PIPERAZINES, PIPERIDINES AND TETRAHYDROPYRIDINES AS SEROTONERGIC AGENTS

This is a divisional of copending application(s) Ser. No. 09/723,478 filed on Nov. 28, 2000 now U.S. Pat. No. 6,376,494, the entire disclosure of which is hereby incorperated by reference which is a continuation-in-part of co-pending U.S. Ser. No. 09/333,153, filed Jun. 14, 1999, now abandon which claims the benefit of U.S. Provisional Application No. 60/135,107, filed Jun. 15, 1998, which was converted from U.S. patent application Ser. No. 09/097,463, pursuant to a petition filed under 37 C.F.R. 1.53(c)(2)(i).

This invention provides compounds which act upon the mammalian 5-$HT_{1A}$ receptor and methods for their use in treating, preventing or ameliorating diseases associated therewith, including anxiety, depression, enhancement of antidepressant activity, schizophrenia, cognitive deficits resulting from neurodegenerative diseases like Alzheimer's Disease, stroke/cerebral ischemia, nausea and vomiting, and in the treatment of prostate cancer and for use in promoting smoking cessation.

BACKGROUND OF THE INVENTION

Compounds having selective partial agonist activity at the 5-$HT_{1A}$ receptor have established a presence in the marketplace as effective anxiolytic agents (buspirone, Buspar®, U.S. Pat. No. 3,717,634). 5-$HT_{1A}$ agonists and antagonists may find use in the treatment of several diseases such as anxiety, depression, enhancement of antidepressant activity, schizophrenia, cognitive deficits resulting from neurodegenerative diseases like Alzheimer's Disease, stroke/cerebral ischemia, nausea and vomiting, and in the treatment of prostate cancer and smoking cessation (for reviews, see: K. Rasmussen and V. P. Rocco, Recent Progress in Serotonin (5-$HT_{1A}$ Receptor Modulators, in *Annual Reports in Medicinal Chemistry*, Volume 30, J. A. Bristol, ed., pp. 1–9 (1995); L. E. Schechter and M. G. Kelly, An overview of 5-HT1A Receptor Antagonists: Historical Perspective and Therapeutic Targets, in *Current Drugs Serotonin ID Research Alert*, 2, 299–309 (1997)).

5-HT1A Agonists/Partial Agonists

Anxiety—The role of serotonin in anxiety has been well established (S. D. Iversen, *Neuropharmacol.*, 23, 15530 (1984); J. E. Barrett and K. E. Vanover, *Psychopharmacol.*, 112, 1 (1993)). 5-$HT_{1A}$ partial agonists and full agonists have demonstrated anxiolytic activity in both preclinical animal models of anxiety (R. J. Rogers, et al., *Pharmacol. Biochem. Behav.*, 48, 959 (1994), P. F. Curle, et al., *Drug Dev. Res.*, 32, 183 (1994); S. E. File and N. Andrews, *Behav. Pharmacol.*, 5, 99 (1994)) and in clinical trials for anxiety (D. S. Chaney, et al., *Ann. Rev. Med.*, 41, 437 (1990); R. D. Chiaie, et al., *J. Clin. Psychopharamacol.*, 15, 12 (1995); L. D. Bedford. *Abstracts. Am. Coll. Neuropsycho-pharmacol.*, San Juan, Puerto Rico, 167 (1994); H. G. M. Westenberg and J. A. Den Boer, *Pharmacopsychiatry*, 26, 30 (1993)).

Depression—There is evidence that 5-$HT_{1A}$ agonists and high-efficacy partial agonists possess antidepressant activity (J. De Vry, *Drug and News Perspectives*, 9, 270 (1996)). This activity is thought to be the result of the drug's ability to exert agonist activity on post-synaptic receptors and desensitize pre-synaptic autoreceptors. Buspirone showed weak antidepressant activity and flexinoxan, a 5-$HT_{1A}$ full agonist, entered clinical trials for depression (A. Sambunaris, et al., *J. Clin. Psychiatry*, 58 (suppl 6), 40 (1997)).

Nausea and Vomiting—Animal studies have shown that 5-$HT_{1A}$ agonists are effective antiemetics against a broad spectrum of conditions, including motion sickness and xylazine- and cis-platinin-induced vomiting (J. B. Lipcot and G. H. Crampton, *Pharmacol. Biochem. Behav.*, 33, 627 (1989)). Flesinoxan, a 5-$HT_{1A}$ full agonist, was found to be particularly active in these models (J. B. Lipcot, *Eur. J. Pharmacol.*, 253, 53 (1994)).

Stroke/Cerebral Ischemia—Glutamate is a predominant neurotransmitter in the central nervous system and has been associated with the ischemia-induced pathophysiology seen in both acute neurodegenerative disorders such as stroke, transient ischemic attack, fetal hypoxia and spinal/brain trauma, and chronic neurodegenerative disorders such as epilepsy, Alzheimer's Disease, amyotrophic lateral sclerosis, Huntingdon's Disease, Parkinson's Disease, AIDS dementia and retinal diseases (W. F. Holt, et al., Glutamate in Health and Disease: The Role of Inhibitors, In *Neuroprotection in CNS Diseases*, P. R. Bar and M. F. Beal, eds., Marcel Dekker, Inc., News York, 1997, pp. 87–119). Therefore, compounds which inhibit or attenuate the release of glutamate represent potential neuroprotective agents. Cerebral ischemia can also result from surgery where the blood flow must be halted for a period of time (e.g., coronary bypass surgery) due to the resulting anoxia and hypoglycemia (J. E. Arrowsmith, et al., A Randomized Trial of Remacemide During Coronary Artery Bypass in 171 Patients, *Stroke*, 29, 2357 (1998)). Compounds which inhibit or attenuate glutamate release would be expected to provide neuroprotection in these scenarios as well.

Serotonin 5-$HT_{1A}$ receptors are located in brain areas which are highly sensitive to ischemia, such as the hippocampus and cerebral cortex. It has been demonstrated that 5-$HT_{1A}$ receptor agonists and partial agonists are able to attenuate glutamate release, most likely through activation of 5-HT1A receptors located on glutamatergic terminals (S. Matsuyama, et al., Regulation of Glutamate Release via NMDA and 5-$HT_{1A}$ Receptors in Guinea Pig Dentate Gyrus, *Brain Res.*, 728, 175 (1996)), and that a number of 5-$HT_{1A}$ agonists and partial agonists exert neuroprotective properties in vivo in animal models (J. De Vry, et al., BAYx3702, *Drugs of the Future*, 22, 341 (1997) and references cited within).

Therefore, compounds Which possess serotonin 5-$HT_{1A}$ agonist or partial activity may be useful as neuroprotective agents for the prevention and/or treatment of ischemia-induced brain damage resulting from acute conditions such as stroke, transient ischemic attack, fetal hypoxia, prolonged cardiac surgery and spinal/brain trauma as well as chronic conditions such as epilepsy, Alzheimer's Disease, amyotrophic lateral sclerosis, Huntingdon's Disease, Parkinson's Disease, AIDS dementia and retinal diseases.

5-HT1A Antagonists

Anxiety—While no clinical trial results have been published, 5-$HT_{1A}$ antagonists have demonstrated anxiolytic activity in several animal models, most notably the elevated plus-maze (D. J. Bill and A. Fletcher, *Br. J. Pharmacol.*, 111, 151P (1994); J.-L. Moreau, et al., *Brain Res. Bull.*, 29, 901 (1992)) and the light/dark box (R. J. Rodgers and J. C. Cole, *Eur. J. Pharmacol.*, 261, 321 (1994). Therefore, 5-$HT_{1A}$ antagonists may find use as anxiolytic agents.

Enhancement of Antidepressant Activity—The 5-$HT_{1A}$ receptor appears to play a major role in mediating antidepressant response (J. F. Deakin, et al., *Trends Pharmacol. Sci.*, 14, 263 (1993). The delay in onset of antidepressant activity seen with serotonin-specific release inhibitors (SSRI's) is a result of the activation of somatodendritic 5-HT$_{1A}$ autoreceptors and a resulting decrease in serotonin release (S. Hjorth and S. B. Auerbach, *Behav. Brain Res.*, 73, 281 (1996). Chronic administration of the SSRI leads to an eventual desensitization of the 5-HT$_{1A}$ autoreceptor, an increase in neuronal firing and serotonin release and concomitant antidepressant activity.

Co-administration of a 5-HT$_{1A}$ antagonist would be expected to inhibit the SSRI-induced activation of presynaptic autoreceptors and, thus, hasten the onset of antidepressant action of SSRI's. This hypothesis is supported by results from studies in animal models using more- or less-specific 5-HT$_{1A}$ antagonists in combination with SSRI's (K. Briner and R. C. Dodel, *Cur. Pharm. Des.*, 4, 291 (1998), and references cited within). Furthermore, clinical trials have shown that co-administration of the 5-HT1A antagonist pindolol significantly reduced the median time needed to achieve a sustained antidepressant response with the SSRI's paroxetine (M. B. Tome, et al., *Int. Clin. Psy.*, 12, 630 (1997) and fluoxetine (V. Perez, et al., *Lancet*, 349, 1594 (1997).

Therefore, 5-HT$_{1A}$ antagonists are expected to enhance the antidepressant activity of SSRI's by reducing the delay in onset of action seen with this class of drugs.

Prostate Cancer—In addition to its role as a neurotransmitter, serotonin can function as a growth factor. Serotonin is found in most neuroendocrine cells of the human prostate, where it may play a role in the progression of prostate carcinoma (P. A. Abrahamsson, et al., *Pathol. Res. Pract.*, 181, 675 (1986); N. M. Hoosein, et al., *J. Urol.*, 149, 479A (1993)). The 5-HT$_{1A}$ antagonist pindobind has shown antineoplastic activity when tested against the human prostate tumor cell lines PC3, DU-145 and LNCaP in vitro and inhibited the growth of the aggressive PC3 cell line in vivo in athymic nude mice (M. Abdul, et al., *Anticancer Res.*, 14, 1215 (1994).

Schizophrenia—Evidence has accumulated over the last decade to suggest that serotonin and various serotonin receptors play a role in the pathophysiology and pharmacological treatment of schizophrenia. Both receptor binding studies (T. Hashimoto, et al., *Life Sci.*, 48, 355 (1991)) and autoradiography (J. N. Joyce, et al., *Neuropsychopharmacol.*, 8, .315 (1993); P.W. J. Bumet, et al., *Neuropsychopharmacol.*, 15, 442 (1996)) on postmortem brains of schizophrenia patients indicate that there is an increase in 5-HT$_{1A}$ receptor density. While the most efficacious antipsychotic treatments to date have targeted dopaminergic neurotransimission, it is clear from binding results that atypical antipsychotics also possess significant serotonergic affinity (H. Y. Meltzer, *Clin. Neurosci.*, 3, 64 (1995). Notably, the 5-HT$_{1A}$ receptor has been associated with changes in dopaminergic neurotransmission (M. Hamon, et al., *J. Pharmacol. Exp. Ther.*, 246, 745 (1988); L. E. Schechter, et al., *J. Pharmacol. Exp. Ther.*, 255, 1335 (1990)). Furthermore, dysfunctional glutamatergic path ways appear to be involved in psychotic pathology and decreased glutamate levels have been demonstrated in schizophrenic brains (K. Q. Do, et al., *J. Neurochem.*, 65, 2652 (1995); G. C. Tsai, et al., *Arch. Gen. Psychiatry*, 52, 829 (1995)). Thus, by enhancing glutamate availability and transmission, 5-HT$_{1A}$ antagonists may function as antipsychotic agents.

Cognitive Deficits from Alzheimer's Disease—Studies on the cholinergic deficits observed in Alzheimer's Disease have made it apparent that not all patients can be characterized by deficits in this in this system alone (P. T. Francis, et al., Neurotransmitters and Neuropeptides, in *Alzheimer's Disease*, R. D. Terry, ed., Raven Press, Ltd., New York, pp. 247–261 (1994)). More recent studies reveal that glutamatergic function is also severely disrupted. Glutamate is an important neurotransmitter that can enhance cognition and physiological phenomena such as long-term potentiation (LTP), which appears to play a role in mediating learning and memory processes. The activation of glutamatergic neurotransmission facilitates memory (U. Stabil, et al., *PNAS (USA)*, 91, 777 (1994)), while glutamate antagonists impair learning and memory as well as LTP in rats (R. G. Morris, et al., *Nature*, 319, 774 (1986); T. V. Bliss and G. L. Collinridge, *Nature*, 361, 31 (1993)).

Studies on the post-mortem brains of Alzheimer's patients have demonstrated reductions in glutamate receptors in both neocortex and hippocampus (J. T. Greenmyre, *Arch. Neurol.*, 43, 1058 (1986); W. F. Marangos, et al., *Trends Neurosci.*, 10, 37 (1987)). Rich in glutamatergic neurons, the pyramidal cell layer of the entorhinal cortex is one of the first areas in the Alzheimer's brain to develop the morphological hallmarks of Alzheimer's Disease, plaques and tangles. Furthermore, there are reduced levels of glutamate in the perforant pathway which projects from the entorhinal cortex to the dentate gyrus (B. T. Hyman, et al., *Ann. Neurol.*, 22, 37 (1987)) and a loss of glutamate staining in the perforant path terminal zone that has been associated with Alzheimer's Disease (N. W. Kowal and M. F. Beal, *Ann. Neurol.*, 29, 162 (1991)). Thus, there is compelling evidence that a deficit in glutamatergic neurotransmission is associated with cognitive impairment and is a pathological finding in Alzheimer's Disease.

Data indicate that 5-HT$_{1A}$ antagonists have a facilitatory effect on glutamatergic neurotransmission (D. M. Bowen, et al., *Trends Neurosci.*, 17, 149 (1994)). Serotonin 5-HT$_{1A}$ antagonists have been shown to both potentiate NMDA-induced glutamate release from pyramidal neurons and significantly elevate glutamate release when administered alone (S. N. Dilk, et al., *Br. J. Pharmacol.*, 115, 1169 (1995)). They inhibit the tonic hyperpolarizing effect of serotonin on neurons in both the cortex and hippocampus, which in turn enhances glutamatergic neurotransmission and signaling (R. Araneda and R. Andrade, *Neuroscience*, 40, 399 (1991)). Coupled with the observation that a functionally hyper-responsive serotonin system in Alzheimer's Disease may contribute to the cognitive disturbances (D. M. McLoughlin, et al., *Am. J. Psychiatry*, 151, 1701 (1994)), the data suggest that 5-HT$_{1A}$ antagonists may improve cognition by removing the inhibitory effects of endogenous serotonin on pyramidal neurons and enhancing glutamatergic activation and the ensuing signal transduction.

Nevertheless, the cholinergic system clearly plays a role in cognitive processing, and recent therapies designed to improve cognition in Alzheimer's patients have been targeted at enhancing cholinergic neurotransmission, either through inhibition of acetylcholinesterase or by the use of agonists. Postsynaptic M1 muscarinic acetylchloline receptors are located on pyramidal neurons along with glutamatergic and 5-HT$_{1A}$ receptor sites. In this regard, blockade of 5-HT$_{1A}$ receptors may compensate for the loss of cholinergic excitatory input by enhancing glutamatergic transduction through the same pathway. In fact, muscarinic (M1) signal transduction may be facilitated by blocking the hyperpolarizing action of serotonin. In addition, there is evidence that 5-HT$_{1A}$ receptor antagonists may decrease the formation of β-amyloid plaques and tangles via its enhancement of muscarinic M1 receptor signaling and resulting activation of protein kinase C (J. D. Baxbaum, et al., *PNAS (USA)*, 90, 9195 (1993)).

Preclinical evidence for treating Alzheimer's Disease has been established using available 5-HT$_{1A}$ antagonists. WAY- 100635 reversed the cognitive deficits induced by fornix lesions in marmosets (J. A. Harder, et al., *Psychopharmacol.*, 127, 245 (1996)). WAY-100135 prevented the impairment of spatial learning caused by intrahippocampal scopolamine, a muscarinic antagonist (M. Carli, et al., *Eur. J. Pharmacol.*, 283, 133 (1995)). NAN-190 has been shown to augment LTP (N. Sakai and C. Tanaka, *Brain Res.*, 613, 326 (1993)). Taken together with the various in vitro data described above and in the literature, these studies strongly suggest that treatment with 5-$HT_{1A}$ receptor antagonists represent a viable strategy for restoring the multiple deficits associated with Alzheimer's Disease.

Smoking Cessation—Cessation from chronic use of nicotine or tobacco in humans results in withdrawal symptoms, including anxiety, irritability, difficulty concentrating and restlessness. These withdrawal symptoms have been shown to play an important role in relapse (J. R. Hughes and D. Hatsukami, *Arch. Gen. Psychiatry*, 43, 289 (1986)). Preclinical evidence indicates that withdrawal from the chronic administration of nicotine increases the sensitivity of 5-$HT_{1A}$ receptors (K. Rasmussen and J. F. Czachura, *Psychopharmacology*, 133, 343 (1997)) and enhances the auditory startle reflex in rats (D. R. Helton, et al., *Psychopharmacology*, 113, 205 (1993)). Serotonin 5-$HT_{1A}$ antagonists have been shown to attenuate this nicotine-withdrawal-enhanced startle response (K. Rasmussen, et al., *Synapse*, 27, 145 (1997); K. Rasmussen, et al., *J. Pharmacol. Exp. Ther.*, 294, 688 (2000)). Thus, 5-$HT_{1A}$ antagonists may find clinical use as a pharmacotherapy for smoking cessation.

DESCRIPTION OF THE INVENTION

In accordance with this invention, there is provided a set of novel compounds, including their enantiomers, which have activity as 5-$HT_{1A}$ agonists and antagonists. Compounds of the present invention are described by the generic formula:

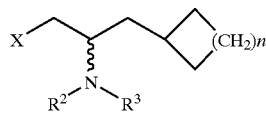

where:

X is selected from the group consisting of:

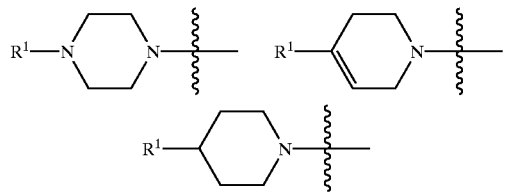

n is selected from the integers 1 through 5;

$R^1$ is $C_6$–$C_{10}$-aryl or mono or bicyclic heteroaryl, optionally substituted by from 1 to 3 substituents, preferably from 1 to 2 substituents selected from the group of F, Cl, Br, I, —OH, —$NH_2$, $CO_2H$, —$CO_2$—$C_1$–$C_6$ alkyl, —CN, —$NO_2$, $C_1$–$C_6$ alkyl, $C_2$–$C_6$ alkenyl, $C_2$–$C_6$ alkynyl, $C_1$–$C_6$ perhaloalkyl, $OR^4$, and $C_1$–$C_6$ perhaloalkoxy, with a proviso that heteroaryl is not thiadiazole;

$R^2$ is selected from the group consisting of H and $C_1$–$C_6$ alkyl;

$R^3$ is selected from the group consisting of H, $COR^5$, $COOR^5$, and $CONR^5R^6$;

$R^4$ is selected from the group consisting of H, $C_1$–$C_6$ alkyl, $C_2$–$C_6$ alkenyl, $C_2$–$C_6$ alkynyl, $C_6$–$C_{10}$ aryl, mono or bicyclic heteroaryl, $C_7$–$C_{14}$ aralkyl, and mono or bicyclic heteroaralkyl, where the aryl or heteroaryl group is optionally substituted with one to three substituents independently selected from the group consisting of F, Cl, Br, I, CN, —$NH_2$, —$NO_2$, —OH, alkyl, $C_2$–$C_6$ alkenyl, $C_2$–$C_6$ alkynyl, $C_1$–$C_6$ perhaloalkyl, $C_1$–$C_6$ alkoxy, and $C_1$–$C_6$ perhaloalkoxy;

$R^5$ and $R^6$ are selected independently from the group consisting of H, $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, adamantyl, and noradamantyl or $R^5$ and $R^6$ taken together with the interposed nitrogen atom may form a 5–7 membered azacyclic ring, optionally containing an additional heteroatom selected from O, S, or $NR^4$; when $R^5$ or $R^6$ are chosen from $C_3$–$C_6$ cycloalkyl or $C_3$–$C_6$ cycloalkenyl, the cyclic group may optionally be substituted at the 1-position with a $C_1$–$C_3$ alkyl group the optical isomers;

and the pharmaceutically acceptable salts thereof

The term $C_6$–$C_{10}$ aryl includes phenyl and naphthyl. Monocyclic heteroaryl means a 5–6 membered heteroaryl group having from 1–3 heteroatoms selected independently from N, O, and S, such as pyridine, pyrrole, thiophene, furan, imidazole, oxazole, pyrimidmne, pyridazine, pyrazine, thiazole and oxathiazole. Bicyclic heteroaryl includes phenyl fused to a monocyclic 5–6 membered heteroaryl group or a 5–6 membered heteroaryl group fused to another 5–6 membered heteroaryl group, including, but not limited to indole, quinoline, isoquinoline, benzofuran, benzodioxan, benzothiophene, benzimidazole, naphthyridine, and imidazopyridine. The term $C_7$–$C_{14}$ aralkyl means a $C_1$–$C_4$ alkyl group having a phenyl or naphthyl group as a substituent, and the term heteroaralkyl means a $C_1$–$C_4$ alkyl group having a mono or bicyclic heteroaryl group as defined above as a substituent.

One group of compounds of this invention includes those of the formula:

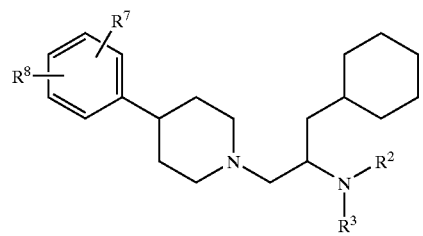

wherein $R^2$ and $R^3$ are as defined above and $R^7$ and $R^8$ are each independently selected from H, F, Cl, Br, I, —OH, —$NH_2$, $CO_2H$, —$CO_2$—$C_1$–$C_6$ alkyl, —CN, —$NO_2$, $C_1$–$C_6$ alkyl, $C_2$–$C_6$ alkenyl, $C_2$–$C_6$ alkynyl, $C_1$–$C_6$ perhaloalkyl, $OR^4$, and $C_1$–$C_6$ perhaloalkoxy; or a pharmaceutically acceptable salt thereof.

Another group of compounds of this invention includes those of the formula:

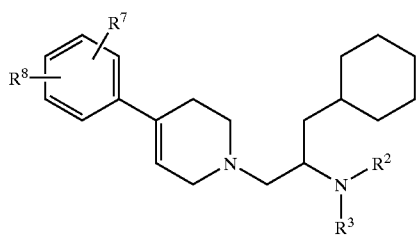

wherein $R^2$, $R^3$, $R^7$ and $R^8$ are as defined above; or a pharmaceutically acceptable salt thereof.

A further group of compounds of this invention includes those of the formula:

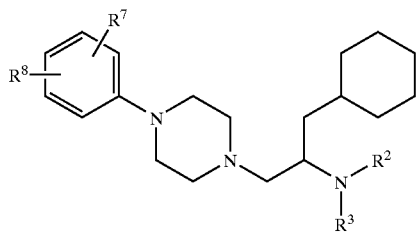

wherein $R^2$, $R^3$, $R^7$ and $R^8$ are as defined above; or a pharmaceutically acceptable salt thereof.

Within each of these groups described herein is a further subset of compounds wherein $R^2$ is H or $C_1$–$C_6$ alkyl and $R^3$ is —C(O)—$C_3$–$C_6$ cycloalkyl, the cyclalkyl ring of which is optionally substituted at the 1-position with a $C_{1-C3}$ alkyl group.

Optical isomers of the invention compounds can be selectively synthesized or separated using conventional procedures known to those skilled in the art of organic synthesis.

The pharmaceutically acceptable salts of the invention compounds include the conventional acid addition salts which are formed from an invention compound and a pharmaceutically acceptable organic or inorganic acid. The acid addition salts include, but is not limited to, the acetate, adipate, alginate, aspartate, benzoate, benzenesulfonate, bisulfate, butyrate, citrate, camphorate, camphorsulfonate, dodecylsulfate, ethanesulfonate, fumarate, glycerophosphate, phosphate, hemisulfate, hydrochloride, hydrobromide, hydroiodide, lactate, maleate, methanesulfonate, nicotinate, oxalate, pamoate, pectinate, pivalate, propionate, succinate, tartrate, and tosylate. Also the basic nitrogen-containing groups may be quaternized with such agents as lower alkyl halides, dialkyl sulfates, long chain halides such as lauryl bromide, aralkyl halides like benzyl and phenethyl bromides.

This invention also provides methods of utilizing the compounds of this invention, or a pharmaceutically acceptable salt thereof, in preventing, treating or ameliorating anxiety, generalized anxiety disorder, depression, schizophrenia, cognitive deficits resulting from neurodegenerative diseases like Alzheimer's Disease, stroke/cerebral ischemia, nausea and vomiting, and in the treatment of prostate cancer. The compounds of this invention can also be used in the treatment, enhancement or facilitation of smoking cessation or in comparable methods of assisting in withdrawal of nicotine-related habits. Each of these methods comprises administering to a mammal in need thereof, preferably a human in need thereof, of a pharmaceutically effective amount of a compound of this invention, or a pharmaceutically acceptable salt thereof.

This invention also provides methods for enhancing the efficacy of selective serotonin reuptake inhibitors (SSRIs) in a mammal, the methods comprising co-administering to a mammal in need thereof pharmaceutically effective amounts of the SSRI in question and a compound of this invention. Among the SSRIs which may be administered in these regimens are fluoxetine hydrochloride, venlafaxine hydrochloride, paroxetine hydrochloride, nefazodone hydrochloride, and sertraline hydrochloride. It will be understood that the SSRIs in these regimens may be administered in dosages and regimens known in the art for these compounds. These methods may also be characterized as methods of treatment of maladies such as depression, anxiety and generalized anxiety disorder in a mammal in need thereof, the methods comprising co-administering to the mammal in need thereof of pharmaceutically effective amounts of a compound of this invention, or a pharmaceutically acceptable salt thereof, and an SSRI.

DETAILED DESCRIPTION OF THE INVENTION

Compounds in which at least one of $R^2$ and $R^3$ is hydrogen are synthesized in four steps (Scheme 1) starting from cycloalkylalanine which has been protected on the nitrogen atom with the t-butoxycarbonyl group (BOC). This material is coupled to the appropriately substituted aryl heterocycle where X is CH, N, or carbon having a double bond to an adjacent carbon atom using dicyclohexylcarbodiimide (DCC) to afford compound 1. Removal of the BOC group under acidic conditions followed by reduction using a borane complex leads to the penultimate intermediate 2. Subsequent acylation of 2 with the appropriate acid chloride gives compound 3, which is isolated as an acceptable salt.

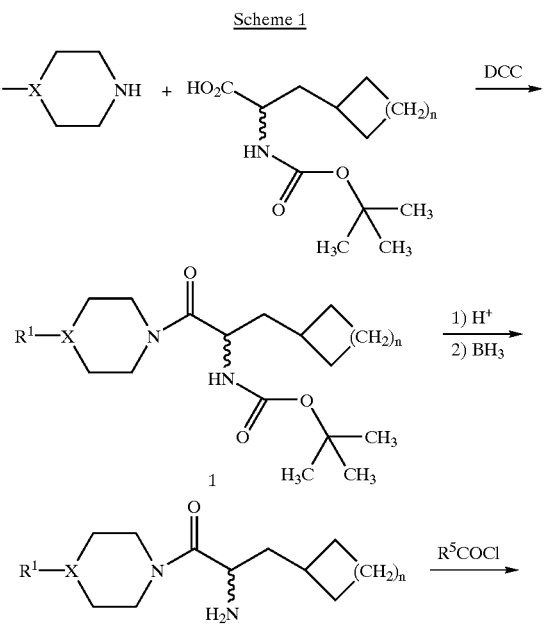

Scheme 1

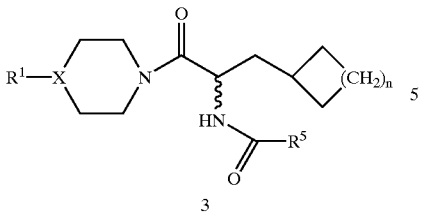

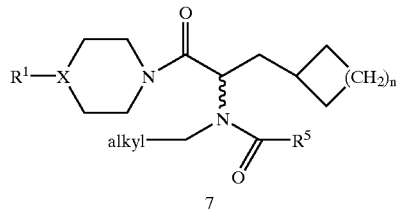

Compounds in which both R² and R³ are other than hydrogen are prepared using two general methods. Reduction of BOC-protected amide 1 with lithium aluminum hydride (LAH) affords methylamine 4 in one step (Scheme 2). Subsequent acylation using the appropriate acid chloride yields N-methylamide 5.

Scheme 2

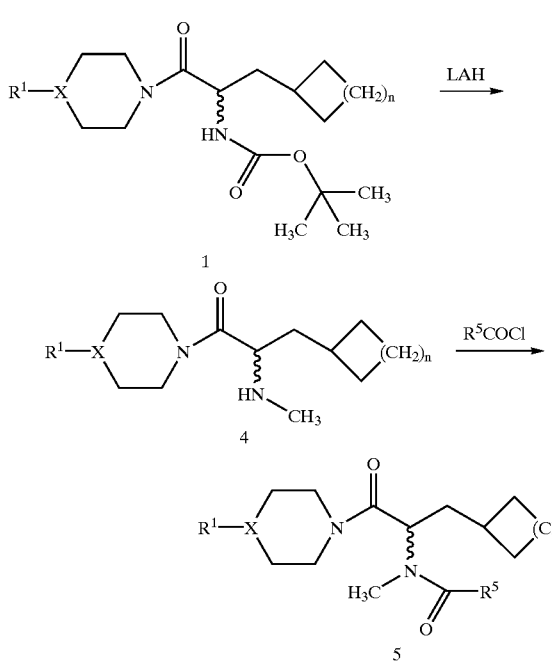

Alternatively, acylation of intermediate 2 followed by reduction with an appropriate reduction agent such as borane dimethylsulfide gives alkylamine 6, which can then be converted to the final acylated product 7 (Scheme 3).

Scheme 3

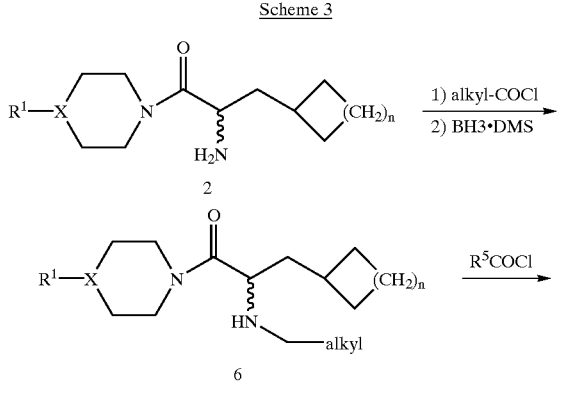

Carbamates and ureas can be prepared from the intermediate amines 2, 4, and 6 either by treatment with an appropriate isocyanate or by reacting the amine with a phosgene equivalent such as trichloromethylchloroformate or triphosgene followed by treatment with an appropriate alcohol or amine. Other synthetic procedures may be apparent to those skilled in the art of organic synthesis.

The compounds of this invention are prepared by conventional methods which are well known to one skilled in the art of chemistry using chemicals that are either commercially available or readily prepared following standard literature procedures. The following examples are included for illustrative purposes only and are not intended to be considered as limiting to this disclosure in any way.

INTERMEDIATES

The preparation of {(1R)-1-cyclohexylmethyl-2-[4-(2-methoxyphenyl)-piperazin-1-yl]-ethyl}-amine exemplifies the synthesis of the analogous penultimate intermediate amines used in the following examples.

{(1R)-1-Cyclohexylmethyl-2-[4-(2-methoxyphenyl)-piperazin-1-yl]-ethyl}-amine To a stirred solution of 2.0 g (7.38 mmol) of (D)-N-(t-butoxycarbonyl)-cyclohexylalanine, 1.42 g (7.38 mmol) of 1-(2-methoxyphenyl)-piperazine, and 1.0 g (7.38 mmol) of 1-hydroxybenztriazole hydrate in 20 ml of dry tetrahydrofuran under a nitrogen atmosphere was added 1.52 g (7.38 mmol) of dicyclohexylcarbodiimide. The resulting mixture was stirred at room temperature under nitrogen overnight. The reaction mixture was then filtered through Celite 545 and concentrated on a rotary evaporator. The desired product, (R)-{1-Cyclohexylmethyl-2-[4-(2-methoxyphenyl)-piperazin-1-yl]-2-oxo-ethyl}-carbamic acid tert-butyl ester (2.90 g, 88% yield), was isolated by chromatography on basic alumina (diethyl ether/methanol) as a yellow solid; mp=69–71° C.; MS FAB m/z=446 (M+H)⁺.

2.75 g (6.20 mmol) of the above-described (R)-{1-Cyclohexylmethyl-2-[4-(2-methoxyphenyl)-piperazin-1-yl]-2-oxo-ethyl}-carbamic acid tert-butyl ester was stirred overnight in a mixture of 30 mL of peroxide-free dioxane and 30 mL of 6N aq. HCl. The resulting yellow mixture was concentrated to dryness on a rotary evaporator and the residue was partitioned between dichloromethane and saturated aq. sodium bicarbonate solution. The aqueous layer was extracted with two additional portions of dichloromethane. The combined organic layers were dried over anhydrous sodium sulfate and concentrated on a rotary evaporator to yield the desired (R)-2-amino-3-cyclohexyl-1-[4-(2-methoxyphenyl)-piperazin-1-yl]-propan-1-one (2.10 g, 98% yield), which was characterized as its dihydrochloride salt by conversion with ethereal HCl to yield the white solid; mp=165–168° C.; MS (+) ESI m/z=346 (M+H)⁺.

The above-described desired (R)-2-amino-3-cyclohexyl-1-[4-(2-methoxyphenyl)-piperazin-1-yl]-propan-1-one (0.83 g, 2.25 mmol) was dissolved in 20 ml of dry toluene and placed in a flame-dried flask under a nitrogen atmosphere. The mixture was heated to reflux and a solution of 0.45 mL of 10M borane-dimethylsulfide complex in 15 mL of dry toluene was added dropwise over ten minutes as reflux was maintained. After complete addition, the reaction mixture was refluxed an additional two hours. The reaction was then cooled to room temperature and 30 mL of 1N aq. HCl was added and the mixture stirred for one hour. Stirring was halted, the mixture was diluted with 20 mL of water and 20 mL of diethyl ether, and the layers were separated. The aqueous layer was washed with an additional 30 mL portion of diethyl ether and then made basic by addition of 50% aq. sodium hydroxide solution. The basic aqueous mixture was then extracted with three 50 mL portions of dichloromethane. The combined organic layers were dried over anhydrous sodium sulfate and concentrated on a rotary evaporator to yield the desired {(1R)-1-cyclohexylmethyl-2-[4-(2-methoxyphenyl)-piperazin-1-yl]-ethyl}-amine (0.74 g, 93% yield) as a yellow oil, which was pure enough to use in subsequent experiments; MS (+) ESI m/z+(M+H)$^+$.

EXAMPLE 1

Cyclohexanecarboxylic Acid {(1R)-1-Cyclohexylmethyl-2-[4-(2-methoxyphenyl)-piperazin-1-yl]-ethyl}-amide To a solution of 0.31 g (0.94 mmol) of {(1R)-1-cyclohexylmethyl-2-[4-(2-methoxyphenyl)-piperazin-1-yl]-ethyl}-amine and 0.26 mL (1.87 mmol) of triethylamine in 10 mL of dichloromethane at 0° C. was added dropwise 0.15 g (1.03 mmol) of cyclohexanecarboxylic acid chloride in 4 mL of dichloromethane. The reaction mixture was allowed to stir under nitrogen at 0° C. for one hour, and was then concentrated on a rotary evaporator, diluted with ethyl acetate and washed with saturated aqueous $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to the dihydrochloride salt of the title compound with ethanolic HCl to yield 0.41 g (85%) as a beige solid; mp=121–131° C.; MS (+) ESI m/z=442 (M+H)$^+$.

Analysis for $C_{27}H_{43}N_3O_2$.2HCl. Calculated: C: 63.02; H: 8.81; N: 8.17. Found: C: 63.56; H: 9.27; N: 8.07.

EXAMPLE 2

1-Methyl-cyclohexanecarboxylic Acid of {(1R)-1-Cyclohexylmethyl-2-[4-(2-methoxyphenyl)-piperazin-1-yl]-ethyl}-amide To a solution of 0.30 g (0.91 mmol) of {(1R)-1-cyclohexylmethyl-2-[4-(2-methoxyphenyl)-piperazin-1-yl]-ethyl}-amine and 0.25 mL (1.74 mmol) of triethylamine in 10 mL of dichloromethane at 0° C. was added dropwise 0.16 g (1.00 mmol) of 1-methyl-cyclohexanecarboxylic acid chloride in 4 mL of dichloromethane. The reaction mixture was allowed to stir under nitrogen at 0° C. for one hour, and was then concentrated on a rotary evaporator, diluted with ethyl acetate and washed with saturated aqueous $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to the hydrochloride.hydrate salt of the title compound with ethanolic HCl to yield 0.30 g (63%) of a light yellow solid; mp=119–121° C.; MS (+) ESI m/z=456 (M+H)$^+$.

Analysis for $C_{28}H_{45}N_3O_2$.HCl.$H_2O$. Calculated: C: 65.92; H: 9.48; N: 8.24. Found: C: 65.85; H: 9.26; N: 7.67.

EXAMPLE 3

Cyclohexanecarboxylic Acid {(1R)-1-Cyclohexylmethyl-2-[4-(2-methoxyphenyl)-piperazin-1-yl]-ethyl}-methyl-amide To a solution of 0.30 g (0.87 mmol) of {(1R)-1-cyclohexylmethyl-2-[4-(2-methoxyphenyl)-piperazin-1-yl]-ethyl}-methyl-amine and 0.25 mL (1.74 mmol) of triethylamine in 10 mL of dichloromethane at 0° C. was added dropwise 0.19 g (1.31 mmol) of cyclohexanecarboxylic acid chloride in 4 mL of dichloromethane. The reaction mixture was allowed to stir under nitrogen overnight at ambient temperature, and was then concentrated on a rotary evaporator, diluted with ethyl acetate and washed with saturated aqueous $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to the dihydrochloride salt with ethanolic HCl to yield 0.41 g (89%) of the title compound as a white solid; mp=222–224° C.; MS (+) ESI m/z=456 (M+H)$^+$.

Analysis for $C_{27}H_{43}N_3O_2$.2HCl. Calculated: C: 63.62; H: 8.96; N: 7.95. Found: C: 63.11; H: 8.81; N: 7.97.

EXAMPLE 4

1-Methyl-cyclohexanecarboxylic Acid {(1R)-1-Cyclohexylmethyl-2-[4-(2-methoxyphenyl)-piperazin-1-yl]-ethyl}-methyl-amide To a solution of 0.30 g (0.87 mmol) of {(1R)-1-cyclohexylmethyl-2-[4-(2-methoxyphenyl)-piperazin-1-yl]-ethyl}-methyl-amine and 0.25 mL (1.74 mmol) of triethylamine in 10 mL of dichloromethane at 0° C. was added dropwise 0.21 g (1.31 mmol) of 1-methyl-cyclohexanecarboxylic acid chloride in 4 mL of dichloromethane. The reaction mixture was allowed to stir under nitrogen overnight at ambient temperature, and was then concentrated on a rotary evaporator, diluted with ethyl acetate and washed with aqueous $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to the dihydrochloride salt of the title compound with ethanolic HCl to yield 0.41 g (86%) of white solid; mp=208–210° C.; MS (+) ESI m/z=470 (M+H)$^+$.

Analysis for $C_{29}H_{47}N_3O_2$.2HCl. Calculated: C: 64.19; H: 9.10, N: 7.74. Found: C: 63.89; H: 9.03; N: 7.93.

EXAMPLE 5

Cyclohexanecarboxylic Acid {(1R)-1-Cyclohexylmethyl-2-[4-(2,3)-dihydrobenzo[1,4]-dioxin-5-yl)-piperazin-1-yl]-ethyl}-methyl-amide To a solution of 0.7 g (1.87 mmol) of {(1R)-1-cyclohexylmethyl-2-[4-(2,3-dihydro-benzo[1,4]dioxin-5-yl)-piperazin-1-yl]-ethyl}-methyl-amine and 0.5 mL (3.7 mmol) of triethylamine in 10 mL of dichloromethane at 0°

C. was added dropwise 0.27 g (1.87 mmol) of cyclohexanecarboxylic acid chloride in dichloromethane. The reaction mixture was allowed to stir under nitrogen overnight at ambient temperature, and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (ethyl acetate/hexanes) and then converted to the hydrochloride.hemihydrate salt of the title compound with ethereal HCl to yield 0.82 g (91%) as a white solid; mp=147–148° C.; MS (+) ESI m/z=484 $(M+H)^+$.

Analysis for $C_{29}H_{45}N_3O_3 \cdot HCl \cdot 0.5H_2O$. Calculated: C: 65.82; H: 8.95; N: 7.94. Found: C: 65.90; H: 9.04; N: 7.98.

EXAMPLE 6

1-Methyl-cyclohexanecarboxylic Acid {(1R)-1-Cyclohexylmethyl-2-[4-(2,3-dihydro-benzo[1,4]dioxin-5-yl)-piperazin-1-yl]-ethyl}-methyl-amide To a solution of 0.7 g (1.87 mmol) of {(1R)-1-cyclohexylmethyl-2-[4-(2,3-dihydro-benzo[1,4]dioxin-5-yl)-piperazin-1-yl]-ethyl}-methyl-amine and 0.5 mL (3.7 mmol) of triethylamine in 10 mL of dichloromethane at 0° C. was added dropwise 0.3 g (1.87 mmol) of 1-methyl-cyclohexanecarboxylic acid chloride in dichloromethane. The reaction mixture was allowed to stir under nitrogen overnight at ambient temperature and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (ethyl acetate/hexanes) and converted to the hydrochloride salt of the title compound with ethereal HCl to yield 0.85 g (91%) of the title compound as a white solid; mp=219–220° C.; MS (+) ESI m/z=498 $(M+H)^+$.

Analysis for $C_{30}H_{47}N_3O_3 \cdot HCl$. Calculated: C: 67.45; H: 9.06; N: 7.87. Found: C: 67.04; H: 9.17; N: 7.88.

EXAMPLE 7

Cyclohexanecarboxylic Acid {(1R)-1-Cyclohexylmethyl-2-[4-(1H-indol-4-yl)-piperazin-1-yl]-ethyl}-methyl-amide To a solution of 0.6 g (1.69 mmol) of {(1R)-1-cyclohexylmethyl-2-[4-(1H-indol-4-yl)-piperazin-1-yl]-ethyl}-methyl-amine and 0.5 mL (3.7 mmol) of triethylamine in 10 mL of dichloromethane at 0° C. was added dropwise 0.25 g (1.69 mmol) of cyclohexanecarboxylic acid chloride in dichloromethane. The reaction mixture was allowed to stir under nitrogen overnight at ambient temperature, and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (ethyl acetate/hexanes) and converted to the hydrochloride.0.3 hydrate salt of the title compound with ethereal HCl yield 0.68 g (87%) as a white solid; mp=>260° C.; MS (+) ESI m/z=465 $(M+H)^+$.

Analysis for $C_{29}H_{44}N_4O \cdot HCl \cdot 0.3H_2O$. Calculated: C: 68.76; H: 9.07; N: 11.06. Found: C: 68.52; H: 9.15; N: 11.18.

EXAMPLE 8

1-Methyl-cyclohexanecarboxylic Acid {(1R)-1-Cyclohexylmethyl-2-[4-)1-indol-4-yl)-piperazin-1-yl]-ethyl}-methyl-amide To a solution of 0.6 g (1.69 mmol) of {(1R)-1-cyclohexylmethyl-2-[4-(1H-indol-4-yl)-piperazin-1-yl]-ethyl}-methyl-amine and 0.5 mL (3.7 mmol) of triethylamine in 10 mL of dichloromethane at 0° C. was added dropwise 0.27 g (1.69 mmol) of 1-methyl-cyclohexanecarboxylic acid chloride in dichloromethane. The reaction mixture was allowed to stir under nitrogen overnight at ambient temperature and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (ethyl acetate/hexanes) and converted to the hydrochloride salt of the title compound with ethereal HCl to yield 0.7 g (87%) as a white solid; mp=253–254° C.; MS (+) ESI m/z=479 $(M+H)^+$.

Analysis for $C_{30}H_{46}N_4O \cdot HCl$. Calculated: C: 69.94; H: 9.20; N: 10.88. Found: C: 69.68; H: 9.21; N: 10.89.

EXAMPLE 9

N-{(1R)-1-Cyclohexylmethyl-2-[4-(2-methoxyphenyl)-piperazin-1-yl]-ethyl}-formamide A mixture of 2.10 mL (23.6 mmol) of glacial acetic acid and 1.23 mL (32.1 mmol) of formic acid was stirred at 60° C. for 4 hours to form the mixed anhydride. The resulting solution was added slowly to an ice-cooled solution of 1.18 g (3.56 mmol) of {(1R)-1-cyclohexylmethyl-2-[4-(2-methoxyphenyl)-piperazin-1-yl]-ethyl}-amine in 35 mL of anhydrous tetrahydrofuran under nitrogen. The reaction mixture was stirred under nitrogen overnight at ambient temperature and was then poured slowly into 60 mL of saturated aqueous $NaHCO_3$ and stirred for 10 minutes. The layers were separated and the aqueous phase was extracted with two additional portions of ethyl acetate. The combined organic phases were dried over anhydrous sodium sulfate, filtered and concentrated on a rotary evaporator to yield the crude product, which was purified by flash chromatography on silica gel (dichloromethane/methanol) and converted to the hydrochloride.1.5 hydrate salt of the title compound with ethanolic HCl to yield 1.03 g (80%) of white solid; mp=157–159° C.; MS (+) ESI m/z=360 $(M+H)^+$.

Analysis for $C_{21}H_{33}N_3O_2 \cdot HCl \cdot 1.5H_2O$. Calculated: C: 59.62; H: 8.81; N: 9.93. Found: C: 59.54; H: 8.63; N: 9.33.

EXAMPLE 10

Cyclohexanecarboxylic Acid {(1R)-1-Cyclohexylmethyl-2-[4-(pyrimidin-2-yl)-piperazin-1-yl]-ethyl}-amide To a solution of 0.2 g (0.66 mmol) of {(1R)-1-cyclohexylmethyl-2-[4-(pyrimidin-2-yl)-piperazin-1-yl]-ethyl}-amine and 0.18 mL (1.32 mmol) of triethylamine in 10 mL of dichloromethane at 0° C. was added dropwise 0.11 g (0.73 mmol) of cyclohexanecarboxylic acid chloride in dichloromethane (2 mL). The reaction mixture was allowed to stir under nitrogen for one hour at 0° C. and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (dichloromethane/methanol) and converted to the hydrochloride salt of the title compound with ethereal HCl to yield 0.21 g (68%) as a white solid; mp=121–123° C.; MS (+) ESI m/z=414 $(M+H)^+$.

Analysis for $C_{24}H_{39}N_5O \cdot HCl \cdot 1.5H_2O$. Calculated: C: 60.42; H: 9.09; N: 14.67. Found: C: 60.75; H: 9.22; N: 14.23.

EXAMPLE 11

Cyclobutane Carboxylic Acid {(1R)-1-Cyclohexylmethyl-2-[4-(pyrimidin-2-yl)-piperazin-1-yl]-ethyl}-amide To a solution of 0.2 g (0.66 mmol) of {(1R)-1-cyclohexylmethyl-2-[4-(pyrimidin-2-yl)-piperazin-1-yl]-ethyl}-amine and 0.18 mL (1.32 mmol) of triethylamine in 10 mL of dichloromethane at 0° C. was added dropwise 0.082 g (0.69 mmol) of cyclobutanecarboxylic acid chloride in dichloromethane (2 mL). The reaction mixture was allowed to stir under nitrogen for two hours at 0° C. and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (dichloromethane/methanol) and converted to the hydrochloride salt of the title compound with ethereal HCl to yield 0.18 g (62%) as a white solid; mp=112–114° C.; MS (+) ESI m/z=386 (M+H)$^+$.

Analysis for $C_{22}H_{35}N_5O.HCl.1.25H_2O$. Calculated: C: 59.44; H: 8.73; N: 15.75. Found: C: 59.66; H: 8.73; N: 15.37.

EXAMPLE 12

Cyclohexane Carboxylic Acid {(1S)-1-Cyclohexylmethyl-2-[4-(6methoxypyridin-2-yl)-piperazin-1-yl]-ethyl}-amide To a solution of 0.2 g (0.60 mmol) of {(12)-1-cyclohexylmethyl-2-[4-(6-methoxypyridin-2-yl)-piperazin-1-yl]-ethyl}-amine and 0.12 mL (1.20 mmol) of triethylamine in 10 mL of dichloromethane at 0° C. was added dropwise 0.092 g (0.63 mmol) of cyclohexanecarboxylic acid chloride in dichloromethane (2 mL). The reaction mixture was allowed to stir under nitrogen for one hour at 0° C. and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (dichloromethane/methanol) and converted to the hydrochloride salt of the title compound with ethereal HCl to yield 0.24 g (82%) as a white solid; mp=107–109° C.; MS (+) ESI m/z=443 (M+H)$^+$.

Analysis for $C_{26}H_{42}N_4O_2.HCl.H_2O$. Calculated: C: 62.82; H: 9.12; N: 11.27. Found: C: 62.75; H: 9.09; N: 11.17.

EXAMPLE 13

Cyclohexanecarboxylic Acid {(1R)-1-Cyclohexylmethyl-2-[4-(benzothiazol-2-yl)-piperazin-1-yl]-ethyl}-amide To a solution of 0.2 g (0.56 mmol) of {(1R)-1-cyclohexylmethyl-2-[4-(benzothiazol-2-yl)-piperazin-1-yl]-ethyl}-amine and 0.16 mL (1.12 mmol) of triethylamine in 10 mL of dichloromethane at 0° C. was added dropwise 0.086 g (0.59 mmol) of cyclohexanecarboxylic acid chloride in dichloromethane (2 mL). The reaction mixture was allowed to stir under nitrogen for one hour at 0° C. and was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (dichloromethane/methanol) and converted to the hydrochloride salt of the title compound with ethereal HCl to yield 0.20 g (70%) as a white solid; mp=229–232° C.; MS (+) ESI m/z=469 (M+H)$^+$.

Analysis for $C_{27}H_{40}N_4OS.HCl.2.5H_2O$. Calculated: C: 58.94; H: 8.43; N: 10.18. Found: C: 59.28; H: 8.62; N: 9.93.

EXAMPLE 14

Cyclohexanecarboxylic Acid {(1R)-1-Cyclohexylmethyl-2-[4-(isoquinolin-1-yl)-piperazin-1-yl]-ethyl}-amide To a mixture of 0.25 g (0.64 mmol) of {(1R)-1-cyclohexylmethyl-2-[4-(isoquinolin-1-yl)-piperazin-1-yl]-ethyl}-amine and 0.145 g (1.05 mmol) of anhydrous potassium carbonate in 10 mL of dichloromethane and 1 mL of water at 0° C. was added dropwise 0.10 g (0.70 mmol) of cyclohexanecarboxylic acid chloride. The reaction mixture was allowed to stir under nitrogen overnight, during which time it came up to room temperature. The phases were separated and the aqueous phase was extracted with four additional 10 mL portions of dichloromethane. The combined organic layers were dried over anhydrous sodium sulfate, filtered and concentrated on a rotary evaporator to yield the crude product, which was purified by flash chromatography on silica gel (dichloromethane/methanol) and converted to the hydrochloride salt of the title compound with isopropanolic HCl to yield 0.17 g (58%) as a white solid; mp=155–159° C.; MS (+) ESI m/z=463 (M+H)$^+$.

Analysis for $C_{29}H_{42}N_4O.2HCl.1.5H_2O$. Calculated: C: 61.90; H: 8.87; N: 9.95. Found: C: 61.78; H: 9.07; N: 9.45.

EXAMPLE 15

Cyclohexanecarboxylic Acid {(1R)-1-Cyclohexylmethyl-2-[4-(2-methoxyphenyl)-piperidin-1-yl]-ethyl}-amide To a solution of 0.076 g of potassium carbonate (0.54 mmol) in 1 ml. of water was added a solution of 0.18 g of {(1R)-1-cyclohexylmethyl-2-[4-(2-methoxyphenyl)-piperidin-1-yl]-ethyl}-amine (0.54 mmol) in 10 mL of dichloromethane. The resulting mixture was cooled to 0° C. and 0.076 mL of cyclohexanecarboxylic acid chloride (0.54 mmol) was added. The reaction was allowed to stir overnight at 0° C., and was then diluted with 5 mL of water and 20 mL of dichloromethane and the phases separated. The aqueous phase was extracted with three additional portions of dichloromethane. The combined organic phases were dried over anhydrous sodium sulfate, filtered and concentrated on a rotary evaporator to yield the crude product, which was purified by flash chromatography on silica gel (dichloromethane/methanol) and converted to the hydrochloride.hydrate salt of the title compound with isopropanolic HCl to yield 0.177 g (68%) of white solid; mp=100–103° C.; MS (+) ESI m/z=441 (M+H)$^+$.

Analysis for $C_{28}H_{44}N_2O_2.HCl.H_2O$. Calculated: C: 67.91; H: 9.56; N: 5.66. Found: C: 68.15; H: 9.57; N: 5.59.

EXAMPLE 16

1-Methyl-cyclohexanecarboxylic acid {(1R)-1-cyclohexylmethyl-2-[4-(2-methoxyphenyl)-piperidin-1-yl]-ethyl}-amide To a solution of 0.076 g of potassium carbonate (0.54 mmol) in 1 ml. of water was added a solution of 0.18 g of {(1R)-1-cyclohexylmethyl-2-[4-(2-methoxyphenyl)-piperidin-1-yl]-ethyl}-amine (0.54 mmol) in 10 mL of dichloromethane. The resulting mixture was cooled to 0° C. and 0.085 g of 1-methyl-cyclohexanecarbonyl chloride (0.54 mmol) was added. The reaction was allowed to stir overnight at 0° C., and was then diluted with 5 mL of water and 20 mL of dichloromethane and the phases separated. The aqueous phase was extracted with three additional portions of dichloromethane, and the combined organic phases were dried over anhydrous sodium sulfate, filtered and concentrated on a rotary evaporator to yield the crude product, which was purified by flash chromatography on silica gel (dichloromethane/methanol) and converted to the hydrochloride.0.75 hydrate salt of the title compound with isopropanolic HCl to yield 0.35 g (55%) as a white solid; mp=208–210° C.; MS (+) ESI m/z=455 (M+H)+.

Analysis for $C_{28}H_{44}N_2O_2.HCl.0.75\ H_2O$. Calculated: C: 69.01; H: 9.69; N: 5.55. Found: C: 69.03; H: 9.60; N: 5.45.

EXAMPLE 17

Cyclohexanecarboxylic Acid {(1R)-1-Cyclohexylmethyl-2-[4-(2-methoxyphenyl)-piperidin-1-yl]-ethyl}-methyl-amide To a solution of 0.080 g of potassium carbonate (0.58 mmol) in 1 ml. of water was added a solution of 0.20 g of {(1R)-1-cyclohexylmethyl-2-[4-(2-methoxyphenyl)-piperidin-1-yl]-ethyl}-methyl-amine (0.58 mmol) in 10 mL of dichloromethane. The resulting mixture was cooled to 0° C. and 0.090 g of cyclohexanecarboxylic acid chloride (0.58 mmol) was added. The reaction was allowed to stir overnight at 0° C., and was then diluted with 5 mL of water and 20 mL of dichloromethane and the phases separated. The aqueous phase was extracted with three additional portions of dichloromethane. The combined organic phases were dried over anhydrous sodium sulfate, filtered and concentrated on a rotary evaporator to yield the crude product, which was purified by flash chromatography on silica gel (dichloromethane/methanol) and converted to the hydrochloride.0.75 hydrate salt of the title compound with isopropanolic HCl to yield 0.195 g (69%) as a white solid; mp=135–137° C.; MS (+) ESI m/z=455 (M+H)+.

Analysis for $C_{29}H_{46}N_2O_2.HCl.0.75\ H_2O$. Calculated: C: 69.01; H: 9.69; N: 5.55. Found: C: 69.07; H: 9.52; N: 5.19.

EXAMPLE 18

1-Methyl-cyclohexanecarboxylic Acid {(1R)-1-Cyclohexylmethyl-2-[4-(2-methoxypheniyl)-piperidin-1-yl]-ethyl}-methyl-amide To a solution of 0.08 g of potassium carbonate (0.58 mmol) in 1 ml. of water was added a solution of 0.18 g of {(1R)-1-cyclohexylmethyl-2-[4-(2-methoxyphenyl)-piperidin-1-yl]-ethyl}-methyl-amine (0.58 mmol) in 10 mL of dichloromethane. The resulting mixture was cooled to 0° C. and 0.093 g of 1-methyl-cyclohexanecarboxylic acid chloride (0.58 mmol) was added. The reaction was allowed to stir overnight at 0° C., and was then diluted with 5 mL of water and 20 mL of dichloromethane and the phases separated. The aqueous phase was extracted with three additional portions of dichloromethane, and the combined organic phases were dried over anhydrous sodium sulfate, filtered and concentrated on a rotary evaporator to yield the crude product, which was purified by flash chromatography on silica gel (dichloromethane/methanol) and converted to the hydrochloride.0.75 hydrate salt of the title compound with isopropanolic HCl to yield 0.220 g (75%) of white solid; mp=169–171° C.; MS (+) ESI m/z=469 (M+H)+.

Analysis for $C_{30}H_{48}N_2O_2.HCl.0.75\ H_2O$. Calculated: C: 69.52; H: 9.82; N: 5.40. Found: C: 69.44; H: 9.61; N: 4.94.

EXAMPLE 19

N-{(1R)-1-Cyclohexylmethyl-2-[4-(2-methoxyphenyl)-piperidin-1-yl]-ethyl}-2,2-dimethyl-propionamide To a solution of 0.076 g of potassium carbonate (0.54 mmol) in 1 ml. of water was added a solution of 0.18 g of {(1R)-1-cyclohexylmethyl-2-[4-(2-methoxyphenyl)-piperidin-1-yl]-ethyl}-amine (0.54 mmol) in 10 mL of dichloromethane. The resulting mixture was cooled to 0° C. and 0.066 g of trimethylacetyl chloride (0.54 mmol) was added. The reaction was allowed to stir overnight at 0° C., and was then diluted with 5 mL of water and 20 mL of dichloromethane and the phases separated. The aqueous phase was extracted with three additional portions of dichloromethane. The combined organic phases were dried over anhydrous sodium sulfate, filtered and concentrated on a rotary evaporator to yield the crude product, which was purified by flash chromatography on silica gel (dichloromethane/methanol) and converted to the hydrochloride.0.75 hydrate salt of the title compound with isopropanolic HCl to yield 0.137 g (56%) of white solid; mp=97–99° C.; MS (+) ESI m/z=415 (M+H)+.

Analysis for $C_{26}H_{42}N_2O_2.HCl.0.75\ H_2O$. Calculated: C: 67.22; H: 9.65; N: 6.02. Found: C: 66.91; H: 9.68; N: 5.90.

EXAMPLE 20

N-{(1R)-1-Cyclohexylmethyl-2-[4-(2-methoxyphenyl)-piperidin-1-yl]-ethyl}-2,2,N-trimethyl-propionamide To a solution of 0.08 g of potassium carbonate (0.58 mmol) in 1 ml. of water was added a solution of 0.20 g of {(1R)-1-cyclohexylmethyl-2-[4-(2-methoxyphenyl)-piperidin-1-yl]-ethyl}-methyl-amine (0.58 mmol) in 10 mL of dichloromethane. The resulting mixture was cooled to 0° C. and 0.075 g of trimethylacetyl chloride (0.62 mmol) was added. The reaction was allowed to stir overnight at 0° C., and was then diluted with 5 mL of water and 20 mL of dichloromethane and the phases separated. The aqueous phase was extracted with three additional portions of dichloromethane. The combined organic phases were dried over anhydrous sodium sulfate, filtered and concentrated on a rotary evaporator to yield the crude product, which was purified by flash chromatography on silica gel (dichloromethane/methanol) and converted to the hydrochloride.0.25 hydrate salt of the title compound with isopropanolic HCl to yield 0.157 g (58%) of white solid; mp=233–236° C.; MS (+) ESI m/z=429 (M+H)+.

Analysis for $C_{27}H_{44}N_2O_2.HCl.0.25\ H_2O$. Calculated: C: 69.05; H: 9.77; N: 5.97. Found: C: 69.28; H: 9.96; N: 5.90.

EXAMPLE 21

1-Methyl-cyclohexanecarboxylic Acid {(1R)-1-Cyclohexylmethyl-2-[4-(2-methoxyphenyl)-3,6-dihydro-2H-pyridin-1-yl]-ethyl}-amide To a solution of 0.25 g (0.76 mmol) of {(1R)-1-cyclohexylmethyl-2-[4-(2-methoxyphenyl)-3,6-dihydro-2H-pyridin-1-yl]-ethyl}-amine and 0.21 mL (1.52 mmol) of triethylamine in 10 mL of dichloromethane at 0° C. was added dropwise 0.13 g (0.84 mmol) of 1-methyl-cyclohexanecarboxylic acid chloride in 4 mL of dichloromethane. The reaction mixture was allowed to stir under nitrogen at 0° C. for one hour, and was then concentrated on a rotary evaporator, diluted with ethyl acetate and washed with saturated aqueous NaHCO$_3$ and brine. The organic phase was dried over anhydrous sodium sulfate, filtered and concentrated on a rotary evaporator to yield the crude product, which was purified by flash chromatography on silica gel (dichloromethane/methanol) and then converted to the hydrochloride.hemihydrate salt of the title compound with ethanolic HCl to yield 0.15 g (41%) of yellow solid; mp=93–95° C.; MS (+) ESI m/z=453 (M+H)$^+$.

Analysis for $C_{29}H_{44}N_2O_2 \cdot HCl \cdot 0.5\ H_2O$. Calculated: C: 69.92; H: 9.31; N: 5.62. Found: C: 69.92; H: 9.03; N: 5.23.

PHARMACOLOGY

Affinity for the serotonin 5-HT$_{1A}$ receptor was established by assaying the test compound's ability to displace [$^3$H] 8-OHDPAT from its binding site on the receptor complex in CHO cells stably transfected with the human 5-HT$_{1A}$ receptor following the procedure described by J. Dunlop, Y. Zhang, D. Smith and L. Schechter (Eur. J. Pharmacol., submitted; variation of a procedure described by J. Zgombick et al., Naunyn-Schmiedeberg's Arch. Pharmacol., 354, 226–236 (1996)). The compounds of this invention displayed high affinity for the 5-HT$_{1A}$ receptor, as described in Table 1.

TABLE 1

| Example | 5-HT$_{1A}$ Affinity (IC$_{50}$) | Agonist Activity cAMP (EC$_{50}$) | Antagonist Activity cAMP (IC$_{50}$) |
| --- | --- | --- | --- |
| Example 1 | 0.57 nM | 0.5 nM | — |
| Example 2 | 1.23 nM | — | 14.6 nM |
| Example 3 | 1.46 nM | — | 4.0 nM |
| Example 4 | 2.82 nM | — | 10.2 nM |
| Example 5 | 2.37 nM | — | 4.6 nM |
| Example 6 | 6.92 nM | — | 7.3 nM |
| Example 7 | 8.84 nM | — | 10.5 nM |
| Example 8 | 32.68 nM | — | — |
| Example 9 | 1.49 nM | — | 17.3 nM |
| Example 10 | 0.71 nM | 1.3 nM | — |
| Example 11 | 2.40 nM | 21.7 nM | |
| Example 12 | 4.14 nM | 14.8 nM | |
| Example 13 | 2.96 nM | 4.8 nM | |
| Example 14 | 1.69 nM | 13.4 mM | |
| Example 15 | 1.08 nM | 3.9 nM | |
| Example 16 | 5.97 nM | — | 46.0 nM |
| Example 17 | 1.69 nM | — | 91.5 nM |
| Example 18 | 5.33 nM | — | 97.5 nM |
| Example 19 | 2.19 nM | — | 40.0 nM |
| Example 20 | 5.00 nM | — | — |
| Example 21 | 2.75 nM | — | 45.5 nM |

Some of the compounds of this invention demonstrated 5-HT$_{1A}$ partial agonist activity, as measured by the test compound's ability to inhibit forskolin-stimulated accumulation of cAMP in CHO cells stably transfected with the human 5-HT$_{1A}$ receptor using a procedure described by J. Dunlop, Y. Zhang, D. Smith and L. Schechter [J. Pharmacol. Tox. Methods, 40, 47–55 (1998); variation of a procedure described by J. Zgombick et al., Naunyn-Schmiedeberg's Arch. Pharmacol., 354, 226–236 (1996)]. Selected compounds of this invention which demonstrated 5-HT$_{1A}$ partial agonist activity in this assay are shown in Table 1.

Some of the compounds of this invention demonstrated 5-HT$_{1A}$ antagonist activity, as measured by the test compound's ability, 1) not to inhibit forskolin-stimulated accumulation of cAMP in CHO cells stably transfected with the human 5-HT$_{1A}$ receptor, and, 2) to completely antagonize the ability of the 5-HT$_{1A}$ full agonist 8-OHDPAT to inhibit the forskolin-stimulated accumulation of cAMP in CHO cells stably transfected with the human 5-HT$_{1A}$ receptor using a procedure described by J. Dunlop, Y. Zhang, D. Smith and L. Schechter [J. Pharmacol. Tox. Methods, 40, 47–55 (1998); variation of a procedure described by J. Zgombick et al., Naunyn-Schmiedeberg's Arch. Pharmacol., 354, 226–236 (1996)]. Selected compounds of this invention which demonstrated 5-HT$_{1A}$ antagonist activity in this assay are shown in Table 1.

PHARMACEUTICAL COMPOSITION

This invention also provides pharmaceutical compositions utilizing the compounds of this invention. Each composition comprises a pharmaceutically or therapeutically effective amount of a compound of this invention and one or more pharmaceutically acceptable carriers or excipients.

A pharmaceutically or therapeutically effective amount of the compounds herein is understood to comprise an amount of the compound(s) in question which will obtain at least a minimum of desired effect in preventing, treating, inhibiting or is managing the symptoms or causes of the malady in question. More preferably, the amount will be the minimum needed to alleviate or remove the undesirable physiological consequences of the malady in question and inhibit or prevent their reoccurrence.

The variables involved in determining a desirable dose for an individual recipient include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of this invention or its pharmaceutically acceptable salt form. The compounds may be administered orally, rectally, parenterally or topically to the skin and mucosa. A daily human dose may be administered from about 0.01–1000 mg/Kg for oral application, preferably 0.5–500 mg/Kg, and 0.1–100 mg/Kg for parenteral application, preferably 0.5–50 mg/Kg.

Applicable solid carriers can include one or more substances which may also act as flavoring agents, lubricants, solubilizers, suspending agents, fillers, glidants, compression aids, binders or tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient in this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferable sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific disease must be subjectively determined by the attending physician. The variables involved include the specific disease state and the size, age and response pattern of the patient.

What is claimed:

1. A method of treating one or more conditions modulated by serotonin $5\text{-HT}_{1A}$ receptors in the central nervous system and in the body of a mammal comprising administering to a mammal having a condition modulated by serotonin $5\text{-HT}_{1A}$ receptors a therapeutically effective amount of a compound according to the formula

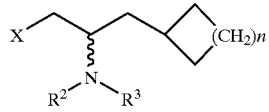

wherein:

X is selected from the group consisting of;

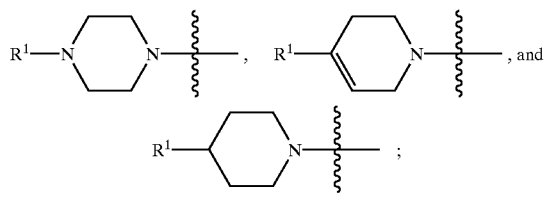

n is selected from the integers 1 through 5;

$R^1$ is $C_6$–$C_{10}$-aryl or mono or bicyclic heteroaryl having 5–10 atoms, 1 to 3 of which are heteroatoms selected independently from N, S or O, wherein the aryl or heteroaryl group is optionally substituted by F, Cl, Br, I, —OH, —NH$_2$, CO$_2$H, —CO$_2$—C$_1$-C$_6$ alkyl, —CN, —NO$_2$, C$_1$-C$_6$ alkyl, C$_2$-C$_6$ alkenyl, C$_2$-C$_6$ alkynyl, C$_1$-C$_6$ perhaloalkyl, OR$^4$, or C$_1$-C$_6$ perhaloalkyl, with a proviso that heteroaryl is not thiadiazole;

$R^2$ is selected from the group consisting of H and $C_1$–$C_6$ alkyl;

$R^3$ is selected from the group consisting of H, COR$^5$, COOR$^5$, and CONR$^5$R$^6$;

$R^4$ is selected from the group consisting of H, C$_1$–C$_6$ alkyl, C$_2$–C$_6$ alkenyl, C$_2$–C$_6$ alkynyl, C$_6$–C$_{10}$ aryl or mono or bicyclic heteroaryl as defined above, C$_7$–C$_{14}$ aralkyl, and mono or bicyclic heteroaralkyl, where the aryl or mono or bicyclic heteroaryl group is as defined above and optionally substituted with one to three substituents independently selected from the group consisting of F, Cl, Br, I, CN, —NH$_2$, —NO$_2$, —OH, alkyl, C$_2$–C$_6$ alkenyl, C$_2$–C$_6$ alkynyl, C$_1$–C$_6$ perhaloalkyl, C$_1$–C$_6$ alkoxy, and C$_1$–C$_6$ perhaloalkoxy;

$R^5$ and $R^6$ are selected independently from the group consisting of H, C$_1$–C$_6$ alkyl, C$_2$–C$_6$ alkenyl, C$_2$–C$_6$ alkynyl, C$_3$–C$_6$ cycloalkyl, C$_3$–C$_6$ cycloalkenyl, adamantyl, and noradamantyl or $R^5$ and $R^6$ taken together with the interposed nitrogen atom may form a 5–7 membered azacyclic ring, optionally containing an additional heteroatom selected from O, S, or NR$^4$; when $R^5$ or $R^6$ are C$_3$–C$_6$ cycloalkyl or C$_3$–C$_6$ cycloalkenyl, the cyclic group may optionally be substituted at the 1-position with a C$_1$–C$_3$ alkyl group;

or an optical isomer thereof, or a pharmaceutically acceptable salt thereof, or both;

with the proviso that when X is

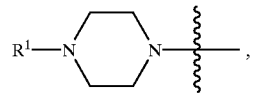

the condition treated is not anxiety or depression.

2. The method according to claim 1 wherein the condition treated is impaired memory or learning or both resulting from one or more neurodegenerative diseases.

3. The method of claim 1, wherein:

$R^1$ is $C_6$–$C_{10}$-aryl or mono or bicyclic heteroaryl, optionally substituted by F, Cl, Br, I, CO$_2$H, —CO$_2$—C$_1$-C$_6$ alkyl, —CN, —NO$_2$, C$_{1-C6}$ alkyl, C$_2$–C$_6$ alkenyl, C$_2$–C$_6$ alkynyl, C$_1$–C$_6$ perhaloalkyl, OR$^4$, or C$_1$–C$_6$ perhaloalkoxy, with a proviso that heteroaryl is not thiadiazole;

$R^4$ is selected from the group consisting of H, C$_1$–C$_6$ alkyl, C$_2$–C$_6$ alkenyl, C$_2$–C$_6$ alkynyl, C$_6$–C$_{10}$ aryl, mono or bicyclic heteroaryl, C$_7$–C$_{14}$ aryl, and mono or bicyclic heteroaralkyl, where the aryl or heteroaryl group is optionally substituted with one to three substituents independently selected from the group consisting of F, Cl, Br, I, CN, —NO$_2$, C$_1$–C$_6$ alkyl, C$_2$–C$_6$ alkenyl, C$_2$–C$_6$ alkynyl, C$_1$–C$_6$ perhaloalkyl, C$_1$–C$_6$ alkoxy, and C$_1$–C$_6$ perhaloalkoxy;

$R^5$ and $R^6$ are selected independently from the group consisting of H, C$_1$–C$_6$ alkyl, C$_2$–C$_6$ alkenyl, C$_2$–C$_6$ alkynyl, C$_3$–C$_6$ cycloalkyl, C$_3$–C$_6$ cycloalkenyl, adamantyl, and noradamantyl or $R^5$ and $R^6$ taken together with the interposed nitrogen atom forms piperidine, morpholine, or piperazine substituted at the 4 position by a substituent selected from R$^4$; when R$^5$ or R$^6$ are chosen from C$_3$–C$_6$ cycloalkyl or C$_3$–C$_6$ cycloalkenyl, the cyclic group may optionally be substituted at the 1-position with methyl group;

or an optical isomer thereof, or a pharmaceutically acceptable salt thereof, or both.

4. The method of claim 1 wherein the compound administered comprises at least one of:

cyclohexanecarboxylic acid {(1R)-1-cyclohexylmethyl-2-[4-(2-methoxyphenyl)-piperazin-1-yl]-ethyl}-amide;

1-methyl-cyclohexanecarboxylic acid {(1R)-1-cyclohexylmethyl-2-[4(2-methoxyphenyl)-piperazin-1-yl]-ethyl}-amide;

cyclohexanecarboxylic acid {(1R)-1-cyclohexylmethyl-2-[4-(2-methoxyphenyl)-piperazin-1-yl]-ethyl}-methyl-amide;

1-1-methyl-cyclohexanecarboxylic acid {(1R)-1-cyclohexylmethyl-2-[4-(2-methoxyphenyl)-piperazin-1-yl]-ethyl}-methyl-amide;

cyclohexanecarboxylic acid {(1R)-1-cyclohexylmethyl-2-[4-((2,3)-dihydrobenzo[1,4]-dioxin-5-yl)-piperazin-1-yl]-ethyl}-methyl-amide;

1-methyl-cyclohexanecarboxylic acid {(1R)-1-cyclohexylmethyl-2-[4-(2,3-dihydro-benzo[1,4]dioxin-5-yl)-piperazin-1-yl]-ethyl}-methyl-amide;

cyclohexanecarboxylic acid {(1R)-1-cyclohexylmethyl-2-[4-(1H-indol-4-yl)-piperazin-1-yl]-methyl-amide;

-methyl-cyclohexanecarboxylic acid {(1R)-1-cyclohexylmethyl-2-[4-(1-indol-4-yl)-piperazin-1-yl]-ethyl}-methyl-amide;

N-{(1R)-1-cyclohexylmethyl-2-[4-(2-methoxyphenyl)-piperazin-1-yl]-ethyl}-formamide;

cyclohexanecarboxylic acid {(1R)-1-cyclohexylmethyl-2-[4-(pyrimidin-2-yl)-piperazin-1-yl]-ethyl}-amide;

cyclobutanecarboxylic acid {(1R)-1-cyclohexylmethyl-2-[4-(pyrimidin-2-yl)-piperazin-1-yl]-ethyl}-amide;

cyclohexanecarboxylic acid {(1S)-1-cyclohexylmethyl-2-[4-(6-methoxypyridin-2-yl)-piperazin-1-yl]-ethyl}-amide;

cyclohexanecarboxylic acid {(1R)-1-cyclohexylmethyl-2-[4-(benzothiazol-2-yl)-piperazin-1-yl]-ethyl}-amide;

cyclohexanecarboxylic acid {(1R)-1-cyclohexylmethyl-2-[4-(isoquinolin-1-yl)-piperazin-1-yl]-ethyl}-amide;

cyclohexanecarboxylic acid {(1R)-1-cyclohexylmethyl-2-[4-(2-methoxyphenyl)-piperidin-1-yl]-ethyl}-amide;

1-methyl-cyclohexanecarboxylic acid {(1R)-1-cyclohexylmethyl-2-[4-(2-methoxyphenyl)-piperidin-1-yl]-ethyl}-amide;

cyclohexanecarboxylic acid {(1R)-1-cyclohexylmethyl-2-[4-(2-methoxyphenyl)-piperidin-1-yl]-ethyl}-methyl-amide;

1-methyl-cyclohexanecarboxylic acid {(1R)-1-cyclohexylmethyl-2-[4-(2-methoxyphenyl)-piperidin-1-yl]-ethyl}-methyl-amide;

N-{(1R)-1-cyclohexylmethyl-2-[4-(2-methoxyphenyl)-piperidin-1-yl]-ethyl}-2,2-dimethyl-propionamide;

N-{(1R)-1-cyclohexylmethyl-2-[4-(2-methoxyphenyl)-piperidin-1-yl]-ethyl}-2,2, N-trimethyl-propionamide; or 1-methyl-cyclohexanecarboxylic acid {(1R)-1-cyclohexylmethyl-2-[4(2-methoxyphenyl)-3,6-dihydro-2H-pyridin-1-yl]-ethyl}-amide;

or an optical isomer thereof, or a pharmaceutically acceptable salt thereof, or both.

5. The method of claim 1 wherein X is

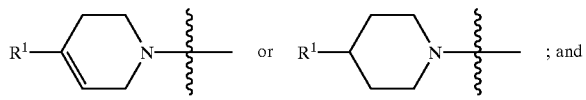

the condition treated is depression or anxiety.

6. The method of claim 1 wherein the condition treated is nausea or vomiting.

7. The method of claim 1 wherein the condition treated is stroke or cerebral ischemia.

8. The method of claim 1 wherein the condition treated is prostate cancer.

9. The method of claim 1 wherein the condition treated is a chronic neurodegenerative disorder selected from Alzheimer's disease, Huntingdon's disease, amyotrophic lateral sclerosis, and Parkinson's disease.

10. The method of claim 1 wherein the condition treated is schizophrenia.

11. The method according to claim 1 wherein the condition treated is nicotine withdrawal.

12. The method of claim 1 further comprising co-administering a serotonin-specific release inhibitor.

* * * * *